United States Patent [19]

Huang et al.

[11] Patent Number: 4,639,466

[45] Date of Patent: Jan. 27, 1987

[54] 3',6-DIISOPENTENYL-2',4'-DIHYDROXY-5,7-DIMETHOXY-ISOFLAVAN AND RELATED COMPOUNDS USEFUL AS ANXIOLYTIC AGENTS AND AVERMECTIN ANTIDOTES

[75] Inventors: Leeyuan Huang, Westfield; Y. K. Tony Lam, Plainsboro, both of N.J.

[73] Assignee: Merck & Co., Inc., Rahway, N.J.

[21] Appl. No.: 656,554

[22] Filed: Oct. 1, 1984

[51] Int. Cl.$^4$ ............................................. A61K 31/35
[52] U.S. Cl. .................................... 514/456; 514/454; 549/406
[58] Field of Search ................. 549/406; 514/456, 454

[56] References Cited

PUBLICATIONS

Ingham, Progress in the Chemistry of Organic Natural Products, 43, 160–181 (1983).
Takashi Kinoshita et al., Chem. Pharm. Bull, 26(1), 141–143 (1978) "A New Isoflavone from Licorice Root".

Primary Examiner—Nicky Chan
Attorney, Agent, or Firm—Theresa Y. Cheng; Michael C. Sudol

[57] ABSTRACT

3',6-Diisopentenyl-2',4'-dihydroxy-5,7-dimethoxyisoflavan has been isolated from *Glycyrrhiza uralensis* Fisch. It has been found that this compound and other related compounds are potent stimulators of benzodiazepine receptors and thereby useful as effective anxiolytic agents. Furthermore, these compounds have been found to be potent antidotes of avermectin.

1 Claim, No Drawings

3',6-DIISOPENTENYL-2',4'-DIHYDROXY-5,7-DIMETHOXY-ISOFLAVAN AND RELATED COMPOUNDS USEFUL AS ANXIOLYTIC AGENTS AND AVERMECTIN ANTIDOTES

BACKGROUND OF THE INVENTION

Benzodiazepines, e.g., diazepam and flunitrazepam, have been widely known as anxiolytic agents acting on the central nervous system (CNS) of man. Recent studies have led to the following observations and conclusions:

(1) Benzodiazepines bind selectively and stereospecifically to particular receptors of brain tissues, especially those located in the cortical regions. Because of this important and well-known discovery, these receptors have been designated as "benzodiazepine receptors."

(2) It has been established that the binding ability of benzodiazepines to these specific receptors in the central nervous system correlates closely with their anxiolytic activity.

(3) Tritium-labelled diazepam ($^3$H-diazepam) of known activity has been used successfully as a label for the benzodiazepine receptors due to its highly efficient and specific binding with the receptors. Since the ability to bind or to compete for the benzodiazepine receptors by a chemical compound parallels its efficacy as an anxiolytic, anticonvulsant or hypnotic agent, the effect of the compound on the $^3$H-diazepam binding has been measured and used in bioassays for the discovery and/or evaluation of antagonists or agonists of the benzodiazepine receptors.

(4) It is known that tracazolate, a known anxiolytic/analgesic also stimulates benzodiazepine binding.

This invention relates to, among other compounds, 3',6-diisopentenyl-2',4'-dihydroxy-5,7-dimethoxyisoflavan which is a potent stimulator to the benzodiazepine receptors and is useful as a minor tranquilizer or a sleeping pill. It is also a potent antidote for various CNS-acting insecticides including (S) α-cyano-3-phenoxybenzyl pyrethroid and avermectin which is also a highly effective antibiotic and antiparasitic agent for mammals.

3',6-Diisopentenyl-2',4'-dihydroxy-5,7-dimethoxyisoflavan has been isolated from a methylene chloride extract of Glycyrrhiza uralensis Fisch. The dried rhizomes and roots of the genus Glycyrrhiza (leguminosae), known as "licorice", have been explored as herbal medicine for peptic ulcer and pharangeal irritation or cough in Asia and Europe.

Accordingly, it is the object of the present invention to provide pure 3',6-diisopentenyl-2',4'-dihydroxy-5,7-dimethoxyisoflavan which is useful as a specific stimulator of benzodiazepine receptors and an antidote for avermectin.

Another object of this invention is to provide processes for the isolation and purification of this novel compound.

A further object of this invention is to provide a pharmaceutically acceptable composition containing 3',6-diisopentenyl-2',4'-dihydroxy-5,7-dimethoxyisoflavan and/or one or more of other active compounds for the treatment of anxiety, intoxication by avermectin and other CNS disorders controlled by the benzodiazepine receptors.

Still a further object of this invention is to provide a method of treatment involving the administration of a therapeutically effective amount of these benzodiazepine receptor stimulators to a patient suffering from various CNS disorders including, for example, anxiety, insomnia, and intoxication caused by CNS-acting insecticides and/or antiparasitic agents such as avermectin.

DETAILED DESCRIPTION OF THE INVENTION

A. The Active Compounds of the Invention

The present invention relates to the active and novel compound of formula

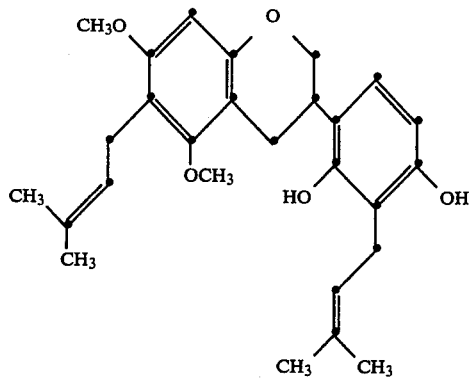

and the following active known compounds: demethylvestitol, vestitol, isovestitol, neovestitol, sativan, isosativan, arvensan, isomucronulatol, mucronulatol, laxifloran, 3-hydroxymaackiainisoflavan, 5-methoxyvestitol, lotisoflavan, 6-methoxyvestitol, bryaflavan, 8-demethylduartin, lonchocarpan, duartin, "machaerol C", "machaerol B", phaseollinisoflavan, glabridin, 2'-o-methylphaseollinisoflavan, 2'-o-methylphaseollidinisoflavan, leiocin, 3'-methoxyglabridin, α, α-dimethylallylcyclolobin, sphaerosinin, unanisoflavan, hispaglabridin A, nitidulin, licoricidin, biscyclolobin, and neoraufavene.

B. Isolation of 3',6-Diisopentenyl-2',4'-dihydroxy-5,7-dimethoxyisoflavan.

$CH_2Cl_2$ extract of G. uralensis (19 g) was flash chromatographed on silica gel 60 (500 g., EM, 230–400 mesh) using 20% $EtOAc/CH_2Cl_2$ as the mobile phase. Benzodiazepine receptor binding assay (BARIN) was employed to monitor the chromatograph. Twenty 200 ml fractions were collected and the active fractions 5 to 15 were pooled and concentrated to yield 9.73 g of crude products. Further purification of this material was achieved by partition chromatography on Sephadex LH-20 (bed vol=3700 ml) in hexanes:toluene:methanol 4:1:1 at a flow rate of 41 ml/min. Activity was recovered at $V_e$=7400–8200 ml, which upon concentration yielded 332 mg of a semipurified product. Preparative thin layer chromatography (EM, silica gel 60F, 20×20 cm. and 2 mm thick) of this material in 5% $MeOH/CH_2Cl_2$ with visualization at 254 nm yielded a UV-absorbing zone of active material ($R_f$=0.56, dry weight=235 mg). Reverse phase preparative high pressure liquid chromatography of this material on a Dupont Zorbax ODS column (2.12×25 cm) using 80% acetonitrile (aq) at a flow rate of 10.6 ml/min and monitoring at 254 nm yielded 12 mg. of an active compound (k'=8) with an $EC_{50}$=2–3 μg/ml. The structure of this active material was determined by ultraviolet/mass spectral and proton magnetic resonance methods to be 3',6-diisopentenyl-2',4'-dihydroxy-5,7-dimethoxyisoflavan.

C. Utility of the compounds within the scope of the invention

This invention also relates to a method of treatment for patients (or mammalian animals raised in the dairy, meat, or fur industries or as pets) suffering from various CNS disorders. More specifically, it relates to a method of treatment involving the administration of one or more of the active compounds described above.

For the treatment of CNS disorders such as anxiety, an active compound may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as horses, cattle, sheep, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets containing the active ingredient in admixture with non-toxic pharmaceutically acceptable excipients may also be manufactured by known methods. The excipients used may be for example, (1) inert diluents such as calcium carbonate, sodium carbonate, lactose, calcium phosphate or sodium phosphate; (2) granulating and disintegrating agents such as corn starch, or alginic acid; (3) binding agents such as starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874 to form osmotic therapeutic tablets for controlled release.

In some cases, formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example peanut oil, liquid paraffin, or olive oil.

Aqueous suspensions normally contain the active materials in admixture with excipients suitable for the manufacture of aqueous suspensions. Such excipients may be (1) suspending agents such as sodium carboxymethylcellulose, methylcellulose, hydroxypropylmethylcellulose, sodium alginate, polyvinylpyrrolidone, gum tragacanth and gum acacia;
(2) dispersing or wetting agents which may be
   (a) a naturally-occurring phosphatide such as lecithin,
   (b) a condensation product of an alkylene oxide with a fatty acid, for example, polyoxyethylene stearate,
   (c) a condensation product of ethylene oxide with a long chain aliphatic alcohol, for example, heptadecaethyleneoxycetanol,
   (d) a condensation product of ethylene oxide with a partial ester derived from a fatty acid and a hexitol such as polyoxyethylene sorbitol monooleate, or
   (e) a condensation product of ethylene oxide with a partial ester derived from a fatty acid and a hexitol anhydride, for example polyoxyethylene sorbitan monooleate.

The aqueous suspensions may also contain one or more preservatives, for example, ethyl or n-propyl p-hydroxybenzoate; one or more coloring agents; one or more flavoring agents; and one or more sweetening agents such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an antioxidant such as ascorbic acid.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example, those sweetening, flavoring and coloring agents described above may also be present.

The pharmaceutical compositions of the invention may also be in the form of oil-in-water emulsions. The oily phase may be a vegetable oil such as olive oil or arachis oils, or a mineral oil such as liquid paraffin or a mixture thereof. Suitable emulsifying agents may be (1) naturally-occurring gums such as gum acacia and gum tragacanth, (2) naturally-occurring phosphatides such as soy bean and lecithin, (3) esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

An active compound may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the anti-inflammatory agents are employed.

Dosage levels of the order from about 0.1 mg to about 100 mg per kilogram of body weight per day are useful in the treatment of the above-indicated conditions (from about 5 mg to about 5 gms. per patient per day).

The amount of active ingredient that may be combined with the carrier materials to produce a single dosage form will vary depending upon the host treated and the particular mode of administration. For example, a formulation intended for the oral administration of humans may contain from 0.5 mg to 5 gm of active agent compounded with an appropriate and convenient amount of carrier material which may vary from about 5 to about 95 percent of the total composition. Dosage unit forms will generally contain between from about 10 mg to about 100 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

D. Biological evidence in support of utility of the invention

1. The C. elegans motility assay:

3',6-Diisopentenyl-2',4'-dihydroxy-5,7-dimethoxyisoflavan was found to be a potent antagonist of avermectin in the C. elegans motility assay (see Table 1 below). This compound at the lowest dose level (5 µg/ml) was almost fully effective in blocking the highest dose of avermectin (0.625 µg/ml).

TABLE 1

| 3',6-diisopentenyl-2',4'-dihydroxy-5,7-dimethoxyisoflavan | avermectin (µg/ml) | | | |
|---|---|---|---|---|
| | 0 | 0.156 | 0.313 | 0.625 |
| 0 | 99 | 85 | 20 | 4 |
| 5 | 97 | 60 | 60 | 77 |
| 25 | 95 | 88 | 65 | 91 |

Effect of 3',6-Diisopentenyl-2',4'-dihydroxy-5,7-dimethoxyisoflavan on avermectin activity in C. elegans (% active worms)

The procedures for the C. elegans motility assay is described in S. S. Pong et al., J. NuroChem. 34, 351-358, 1980.

2. The Benzodiazepine Receptor Binding Assay:

3',6-Diisopentenyl-2',4'-dihydroxy-5,7-dimethoxyisoflavan was found to stimulate the benzodiazepine-binding ($EC_{50} = 3$ µg/ml). The procedures for the benzodiazepine receptor binding assay are essentially the same as those described by M. Williams, Life Sciences, 24, 833-842 (1979).

What is claimed is:

1. A method of treatment or management of CNS disorders mediated by benzodiazepine receptors and intoxication caused by avermectin comprising the administration to a mammalian species in need of such treatment an effective amount of a compound of structural formula:

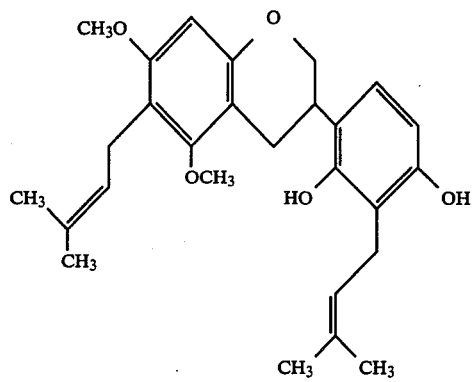

* * * * *